United States Patent
Devaux et al.

(10) Patent No.: US 12,428,368 B2
(45) Date of Patent: Sep. 30, 2025

(54) PROCESS FOR MANUFACTURING AMINOUNDECANOIC ACID AND AMINODECANOIC ACID

(71) Applicant: Arkema France, Colombes (FR)

(72) Inventors: Jean-François Devaux, Pierre-Benite (FR); Myriam Gerbier, Pierre-Benite (FR); Jean-Michel Bossoutrot, Pierre-Benite (FR); Jose Luis Orozco, Pierre-Benite (FR)

(73) Assignee: ARKEMA FRANCE, Puteaux (FR)

( * ) Notice: Subject to any disclaimer, the term of this patent is extended or adjusted under 35 U.S.C. 154(b) by 208 days.

(21) Appl. No.: 18/002,164

(22) PCT Filed: Jun. 16, 2021

(86) PCT No.: PCT/FR2021/051080
§ 371 (c)(1),
(2) Date: Dec. 16, 2022

(87) PCT Pub. No.: WO2021/255387
PCT Pub. Date: Dec. 23, 2021

(65) Prior Publication Data
US 2024/0083838 A1    Mar. 14, 2024

(30) Foreign Application Priority Data
Jun. 18, 2020  (FR) ..................... 2006390

(51) Int. Cl.
*C07C 227/08* (2006.01)
*C07C 227/40* (2006.01)

(52) U.S. Cl.
CPC .......... *C07C 227/08* (2013.01); *C07C 227/40* (2013.01)

(58) Field of Classification Search
None
See application file for complete search history.

(56) References Cited

U.S. PATENT DOCUMENTS

| | | | |
|---|---|---|---|
| 2,070,263 | A | 2/1937 | Dressel et al. |
| 2,772,302 | A | 11/1956 | Werner et al. |
| 4,859,644 | A | 8/1989 | Van et al. |
| 8,013,251 | B2 | 9/2011 | Bhandari et al. |
| 2005/0004326 | A1 | 1/2005 | Seargeant |
| 2009/0292073 | A1 | 11/2009 | Richter et al. |
| 2010/0105812 | A1 | 4/2010 | Bussi et al. |
| 2016/0185705 | A1 | 6/2016 | Berthe et al. |
| 2017/0242372 | A1 | 8/2017 | Omori et al. |
| 2018/0155497 | A1 | 6/2018 | Quinn et al. |

FOREIGN PATENT DOCUMENTS

| | | |
|---|---|---|
| CN | 1218796 A | 6/1999 |
| CN | 103804209 A | 5/2014 |
| CN | 109843976 A | 6/2019 |
| EP | 0235866 A2 | 9/1987 |
| EP | 3030543 B1 | 7/2018 |
| FR | 928265 A | 11/1947 |
| FR | 951932 A | 11/1949 |
| FR | 958178 A | 3/1950 |
| JP | 2012512850 A | 6/2012 |
| JP | 2018531240 A | 10/2018 |
| TW | 200906907 A | 2/2009 |
| WO | 2018080869 A1 | 5/2018 |

OTHER PUBLICATIONS

International Search Report (PCT/ISA/210) with translation and Written Opinion (PCT/ISA/237) mailed on Oct. 1, 2021, by the European Patent Office as the International Searching Authority for International Application No. PCT/FR2021/051080. (9 pages).
Search Report issued on Dec. 13, 2022, in corresponding Taiwanese Patent Application No. 110122191, (1 page).
Decision to Grant a Patent in Japanese Application No. 2022577597 dated Jun. 17, 2025, with English Abstract, 5 pages.

*Primary Examiner* — Amy C Bonaparte
(74) *Attorney, Agent, or Firm* — Boone IP Law

(57) ABSTRACT

Process for producing aminocarboxylic acid of formula (I): $NH_3-CH_2-(CH_2)_n-COOH$ (I) including: (i) reacting the unsaturated carboxylic acid of formula (II): $CH=CH-(CH_2)_{n-1}-COOH$ (II) with hydrogen bromide to form the ω-bromoalkanoic acid of formula (iii): $Br-CH_2-(CH_2)_n-COOH$ (III); (ii) reacting the ω-bromoalkanoic acid obtained with ammonia in aqueous solution to form a reaction mixture; (iii) separating the reaction mixture of the aminocarboxylic acid of formula (I) and an aqueous solution rich in ammonium bromide; (iv) bringing the aqueous solution rich in ammonium bromide into contact with sodium hydroxide to form ammonia and an aqueous solution rich in sodium bromide; (v) purifying the aqueous solution rich in sodium bromide; (vi) bringing the purified aqueous solution rich in sodium bromide into contact with chlorine to form bromine and an aqueous solution rich in sodium chloride; (vii) reacting the bromine with hydrogen to form hydrogen bromide; and (viii) recycling the hydrogen bromide to step (i).

16 Claims, No Drawings

PROCESS FOR MANUFACTURING AMINOUNDECANOIC ACID AND AMINODECANOIC ACID

TECHNICAL FIELD

The present patent application relates to a process for manufacturing aminocarboxylic acids, notably 10-aminodecanoic acid, 11-aminoundecanoic acid and 12-aminododecanoic acid. It also relates to a process for producing polyamide or copolyamide from said aminocarboxylic acids.

PRIOR ART

Aminocarboxylic acids such as 10-decanoic acid, 11-aminoundecanoic acid and 12-aminododecanoic acid are monomers of use in particular in the manufacture of long-chain polyamides such as polyamide 10, polyamide 11 and polyamide 12, respectively.

The excellent thermal and mechanical properties of these polyamides and also their chemical resistance make them advantageous for various applications, notably in motor vehicles, sports equipment, coatings or 3-D printing. One increasingly valued advantage of these polyamides is the fact that their monomers can be obtained from products of plant origin and that are therefore renewable.

Thus, 11-aminoundecanoic acid is attainable from castor oil by transesterification in the presence of methanol and subsequent pyrolysis. The methyl 10-undecenoate obtained is hydrolysed to 10-undecenoic acid which can be brominated at the chain end by a step of hydrobromination. The 11-bromoundecanoic (or ω-bromoundecanoic) acid obtained can then be subjected to a step of ammonolysis by reaction with ammonia to give 11-aminoundecanoic acid and ammonium bromide.

The hydrobromination step is described for example in French patent FR 928265 A. Hydrobromic acid is made to act on 10-undecenoic acid in solution in an organic solvent in the presence of a catalyst such as benzoyl peroxide.

French patent FR 951932 proposes to increase the yield of 11-bromoundecanoic acid to around 80% using hydrobromic acid in excess and a hydrocarbon solvent such as benzene, toluene, petroleum ether or chlorinated hydrocarbons.

According to European patent EP 3 030 543 B1, it is also possible to use other solvents when the reaction is carried out in two steps, the first step consisting in mixing, in a first reactor, 10-undecenoic acid and hydrobromic acid in the form of a liquid stream in turbulent flow and the second step consisting in continuing the reaction in a second reactor in transitional or laminar flow. Patent applications FR 928265 and EP 235 866 B1 describe the conversion of 11-bromoundecanoic acid to 11-aminoundecanoic acid by treatment with an aqueous solution of ammonium hydroxide. The 11-aminoundecanoic acid formed is separated from the ammonium bromide formed.

Application WO 2018/080869 A1 describes the synthesis of 10-aminodecanoic acid from 9-decenoic acid obtained from a palm oil composition. In particular, the hydrobromination of 9-decenoic acid is carried out by bubbling gaseous hydrogen bromide through a solution of 9-decenoic acid in toluene in the presence of benzoyl peroxide at a temperature of from 5° C. to 15° C. After washing, drying and purification in hexane, the yield of 10-bromodecanoic acid is 64%. The 10-bromodecanoic acid can react with 28% ammonium hydroxide at ambient temperature then at 45° C. to form 10-aminodecanoic acid, which is recovered by crystallization at ambient temperature then filtration, washing and drying.

It is known to those skilled in the art that 11-dodecenoic acid, manufactured from 10-undecenoic acid, can react with hydrogen bromide in the presence of benzoyl hydroperoxide to give 12-bromododecanoic acid with a yield of 88% (see Chemistry & Industry (London) 1954, 190-191). All of these processes have the drawback of requiring substantial amounts of hydrogen bromide, generally produced on-site by expensive reaction of bromine with hydrogen, and of producing large amounts of salt-laden effluents.

It is known to convert the ammonium bromide obtained in the ammonolysis step to hydrogen bromide, via a conversion to sodium bromide then to bromine, which is then reacted with hydrogen (see Kunststoff Handbuch, Polyamide, 3/4, published by L. Bottenbruch and R. Binsack, Hanser Fachbuchverlag 1998, pp. 646-648).

Despite the progress, there still remains a need to improve this process. In particular, low yields are observed for the conversion of sodium bromide to bromine and fouling is observed during the conversion of the bromine thus obtained to hydrogen bromide.

SUMMARY OF THE INVENTION

The objective of the invention is therefore to propose a process for manufacturing aminocarboxylic acids, in particular 12-aminododecanoic acid, 11-aminoundecanoic acid and 10-aminodecanoic acid, which is more economical and makes it possible to reduce the amount of effluents.

Specifically, the present invention is based on the observation that it is possible to reduce the amount of bromine required for the process and also the amount of bromides discharged into the environment by replacing a portion of the bromine with chlorine.

Furthermore, it has been discovered that a step of purifying the sodium bromide before the conversion to bromine made it possible to substantially reduce the fouling of the reactor during the conversion to hydrogen bromide.

Therefore, according to a first aspect, one subject of the invention is a process for producing aminocarboxylic acid of formula (I) below:

$$NH_2—CH_2—(CH_2)_n—COOH \qquad (I)$$

in which n is an integer from 7 to 12, preferably from 8 to 10, comprising the following steps:

(i) reacting the unsaturated carboxylic acid of formula (II) below:

$$CH_2=CH—(CH_2)_{n-1}—COOH \qquad (II)$$

with hydrogen bromide (HBr) to form the ω-bromoalkanoic acid of formula (III) below:

$$Br—CH_2—(CH_2)_n—COOH \qquad (III)$$

(ii) reacting the ω-bromoalkanoic acid of formula (III) obtained with ammonia in aqueous solution to form a reaction mixture comprising the aminocarboxylic acid of formula (I) and ammonium bromide;

(iii) separating the reaction mixture of the aminocarboxylic acid of formula (I) and an aqueous solution rich in ammonium bromide;

(iv) bringing the aqueous solution rich in ammonium bromide obtained into contact with sodium hydroxide to form ammonia and an aqueous solution rich in sodium bromide;

(v) purifying the aqueous solution rich in sodium bromide obtained in order to eliminate the organic impurities;
(vi) bringing the purified aqueous solution rich in sodium bromide obtained into contact with chlorine to form bromine and an aqueous solution rich in sodium chloride;
(vii) reacting the bromine obtained with hydrogen to form hydrogen bromide; and
(viii) recycling the hydrogen bromide obtained to step (i).

According to one embodiment, bromides originating from another process are added to the solution rich in ammonium bromide or sodium bromide of step (iv). According to another embodiment, bromine originating from another process is added to the bromine obtained in step (vi).

According to one embodiment, step (v) of purifying the aqueous solution of bromides makes it possible to reduce the TOC (total organic carbon) by a factor of more than 5. According to another embodiment, step (vi) is performed with a bromide solution having less than 2%, and preferably less than 1% of TOC and more preferentially less than 0.5% of TOC.

According to a first embodiment of the process that is the subject of the invention, step (v) is carried out by acidification of the aqueous solution rich in sodium bromide resulting from step (iv) followed by a decantation of the oily phase formed. Preferably, the aqueous solution rich in sodium bromide resulting from step (iv) is acidified by addition of acid to a pH of between 3 and 5. Advantageously, step (v) comprises a subsequent step (va) in which the oily phase formed in step (v) is subjected to an extraction operation to obtain an aqueous solution enriched in sodium bromide, which is sent back to step (iv) or (vi). Advantageously, the operation that makes it possible to extract an aqueous solution enriched in sodium bromide in step (va) is a liquid/liquid extraction.

According to a second embodiment of the process that is the subject of the invention, step (v) is carried out by neutralization of the aqueous solution rich in sodium bromide followed by a liquid/liquid extraction. Preferably, the aqueous solution rich in sodium bromide is neutralized in step (v) to a pH of between 3 and 10. Advantageously, the neutralization in step (v) is carried out by addition of an aqueous solution of hydrochloric acid, of hydrobromic acid, of sulfuric acid or of a mixture thereof.

According to a third embodiment of the process that is the subject of the invention, step (v) is carried out by adsorption on an adsorbent material. Preferably, the adsorption material is chosen from mineral materials such as activated carbon; a silica or an alumina or a mixture thereof; organic materials such as adsorbent macrocrosslinked resins or ion-exchange resins.

According to a fourth embodiment of the process that is the subject of the invention, step (v) is carried out by membrane separation to form a permeate enriched in sodium bromide and depleted in organic impurities and a concentrate depleted in sodium bromide and enriched in organic impurities. Step (v) may be carried out notably by means of one or more nanofiltration membranes.

Advantageously, step (v) comprises a subsequent step (va') in which the concentrate depleted in sodium bromide and enriched in organic impurities which is obtained in step (v) is subjected to a step of diafiltration in order to recover an aqueous solution enriched in sodium bromide and depleted in organic impurities, which solution will be able to be mixed with the permeate resulting from step (v).

Furthermore, step (v) may comprise a subsequent step (vb) in which the permeate enriched in sodium bromide and depleted in organic impurities which is obtained in step (v) and also, where appropriate, the aqueous solution enriched in sodium bromide and depleted in organic impurities resulting from step (va') are subjected to a second step of membrane separation.

According to another aspect, the invention also relates to a process for producing polyamide or copolyamide from said aminocarboxylic acid.

DESCRIPTION OF THE EMBODIMENTS

Definition of the Terms

The term "bromide" is understood to denote generally a compound comprising a bromine atom in the (—I) oxidation state devoid of a carbon-hydrogen bond, such as a bromide salt, notably an alkali metal bromide such as sodium bromide or potassium bromide, ammonium bromide or else hydrogen bromide or hydrobromic acid.

As mentioned above, the object of the present invention is to improve the economics of the process for producing aminocarboxylic acids such as 12-aminododecanoic acid, 11-aminoundecanoic acid or 10-aminodecanoic acid by reducing, or even preventing the provision of bromine and the fouling during the conversion of the bromine thus obtained to hydrogen bromide.

According to the invention, the process for producing an aminocarboxylic acid of formula (I) below:

$$NH_2-CH_2-(CH_2)_n-COOH \quad (I)$$

in which n is an integer from 7 to 12, preferably from 8 to 10, comprises the following steps:
(i) reacting the unsaturated carboxylic acid of formula (II) below:

$$CH_2=CH-(CH_2)_{n-1}-COOH \quad (II)$$

with hydrogen bromide (HBr) to form the ω-bromoalkanoic acid of formula (III) below:

$$Br-CH_2-(CH_2)_n-COOH \quad (III)$$

(ii) reacting the ω-bromoalkanoic acid of formula (III) obtained with ammonia in aqueous solution to form a reaction mixture comprising the aminocarboxylic acid of formula (I) and ammonium bromide;
(iii) separating the reaction mixture of the aminocarboxylic acid of formula (I) and an aqueous solution rich in ammonium bromide;
(iv) bringing the aqueous solution rich in ammonium bromide obtained into contact with sodium hydroxide to form ammonia and an aqueous solution rich in sodium bromide;
(v) purifying the aqueous solution rich in sodium bromide obtained in order to eliminate the organic impurities;
(vi) bringing the purified aqueous solution rich in sodium bromide obtained into contact with chlorine to form bromine and an aqueous solution rich in sodium chloride;
(vii) reacting the bromine obtained with hydrogen to form hydrogen bromide; and
(viii) recycling the hydrogen bromide obtained to step (i).

As explained above, a certain number of unsaturated carboxylic acids of formula (II) such as 11-dodecenoic acid and 10-undecenoic acid and 9-decenoic acid used in the process may be obtained from renewable sources such as plant oils.

11-Dodecenoic acid may be obtained by reduction of 10-undecenoic acid to undecenol, then the conversion to undecenyl bromide, then treatment with sodium cyanide and hydrolysis of the nitrile formed.

10-Undecenoic acid may be obtained from castor oil by the following steps: methanolysis to form methyl ricinoleate, pyrolysis to methyl 10-undecenoate and heptanal, then the hydrolysis of the methyl 10-undecenoate. 10-Undecenoic acid may also be obtained by pyrolysis of ricinoleic acid obtained by hydrolysis of castor oil. Methyl ricinoleate may also be obtained by reactive trituration of castor seeds.

9-Decenoic acid may be obtained from esters of fatty acids derived from natural oils for example by reaction with an alpha-olefin in the presence of a catalyst and hydrolysis of the ester of 9-decenoic acid obtained to 9-decenoic acid, as described in WO 2018/080869.

Step (i)

The reaction of the unsaturated carboxylic acid of formula (II) with hydrogen bromide (HBr) according to step (i) of the process of the invention to form the ω-bromoalkanoic acid of formula (III) is known to those skilled in the art and is described for example in FR 951.932, U.S. Pat. No. 2,772, 302, EP 3 030 543 B1, CN 103804209 B or WO 18/080869.

The unsaturated carboxylic acid of formula (II) is preferably used in liquid form, in particular molten or dissolved in a solvent or a mixture of solvents.

The HBr may be in gas or liquid form, for example liquefied under its saturation vapour pressure or in solution in a solvent or mixture of solvents.

When a solvent is used in the process of the invention, the solvent is preferably chosen from: benzene, fluorobenzene, chlorobenzene, toluene, α,α,α-trifluorotoluene, ethylbenzene, xylenes, cyclohexane, methylcyclohexane, methylcyclopentane, n-hexane, 2-methylhexane, 3-methylhexane, n-heptane, isooctane, tetrachloroethylene, 1,1,1-trichloroethane, dibromomethane, trichloromethane, tetrachloromethane, 1-bromopropane, dimethyl carbonate, tetrahydrofuran (THF), 1,4-dioxane, 2-methyltetrahydrofuran, tetrahydropyran (THP), 1-propoxypropane, 1-ethoxybutane, 2-isopropoxypropane, acetonitrile, and mixtures thereof.

Advantageously, the optional solvent(s) are heated to a temperature in the range from −50° C. to 30° C., preferably from −40° C. to 10° C., preferably from −30° C. to 0° C., preferably from −30° C. to −10° C.

The reaction is generally carried out with HBr in molar excess relative to the unsaturated carboxylic acid of formula (II).

The reaction is usually carried out in the presence of a radical initiator. The radical initiator is a radical generator which may be chosen in particular from oxygen or an oxygen-containing gas such as air or oxygen-enriched air, a peroxide such as for example benzoyl peroxide, or UV radiation. Due to its ease of industrial processing, its stability, and its lower cost compared with the other types of initiators, oxygen or an oxygen-containing gas is particularly preferred.

The hydrobromination may be carried out in a homogeneous liquid medium, or else in a liquid-gas phase.

The reaction may be carried out in a packed column reactor, a stirred reactor or a tubular reactor.

The reaction mixture leaving the reactor may undergo an evaporation of the excess HBr or may be washed with water to remove the residual HBr. After the evaporation of the optional solvent and purification if necessary, the ω-bromoalkanoic acid of formula (III) is obtained.

Steps (ii) and (iii)

In step (ii) of the process of the invention, the ω-bromoalkanoic acid of formula (III) thus obtained is reacted with ammonia, which step is referred to as an ammonolysis step. Step (iii) of the process of the invention consists in separating the aminocarboxylic acid of formula (I) formed from the reaction mixture. The separation may be carried out in particular by solid-liquid separation. The product is then purified, in particular by washing with water or an aqueous solution. In this way aqueous solutions rich in ammonium bromide are obtained.

These steps (ii) and (iii) are known to those skilled in the art and are described for example in FR 928.265, FR 958.178, CN 1078585 C, CN 103804209B or WO 18/080869.

It is possible to use liquefied ammonia or ammonium hydroxide in aqueous, alcoholic or aqueous-alcoholic solution. The reaction may be carried out at low temperature, for example at ambient temperature or 30° C., or at higher temperature, for example 80° C. Depending on the temperature chosen, the reaction time may vary between 5 and 120 hours approximately, the yield being lower at higher temperature. Advantageously, the reaction medium is subjected to a regular temperature rise between an initial temperature of 15° C. to 25° C. and a final temperature of 26° C. to 40° C. The pressure may be atmospheric pressure or close thereto.

The ammonolysis reaction may be carried out in a stirred reactor or in a battery of 2 to 25 stirred reactors in series or in parallel.

The aminocarboxylic acid of formula (I) formed may be separated from the reaction mixture for example via the following steps. The reaction mixture is diluted in water and heated to boiling. The ammonia which is released is collected in water to form an ammonium hydroxide solution, which can be reused in particular for supplying the ammonia used in step (ii). The mixture is then separated from the optional oil layer formed by hot decantation before being cooled in order to separate the 12-aminododecanoic acid, 11-aminoundecanoic acid or 10-aminodecanoic acid by crystallization. The solid is drained, washed with water and optionally recrystallized in boiling water.

The mother liquors collected during the separation and the purification of the intended product contain ammonium bromide and constitute the solution rich in ammonium bromide which will be treated subsequently in the process of the invention.

The aminocarboxylic acid of formula (I) may also be separated from the ammonolysis reaction mixture by solid/liquid separation such as filtration on a filter or draining. The mother liquors collected may undergo a liquid-liquid extraction, a crystallization and/or a filtration in order to form an aqueous solution rich in ammonium bromide and depleted in the aminocarboxylic acid of formula (I).

Step (iv)

In step (iv), the aqueous solution rich in ammonium bromide formed from the mother liquors obtained in the preceding step is reacted with sodium hydroxide to convert the ammonium bromide into sodium bromide, with evolution of ammonia in gaseous form.

This reaction may be carried out for example in a stirred reactor or a packed column.

The amount of sodium hydroxide added will advantageously be approximately stoichiometric relative to the amount of ammonium ions. A very satisfactory result is obtained with sodium hydroxide added in a molar ratio of 1:0.8 to 1:1.25 relative to the content of ammonium ions in the solution. Advantageously, the amount of sodium hydroxide added in this step is a stoichiometric amount or a slightly excess amount, for example a molar ratio of 1:1.0 to 1:1.1 relative to the content of ammonium ions in the solution.

The sodium hydroxide may be added in solid form or in the form of a solution, in particular an aqueous solution. Advantageously, a concentrated aqueous solution of sodium hydroxide is used in order to reduce water consumption. The use of sodium hydroxide in the form of a solution having a content of from 2 to 20 mol/l, and in particular from 6 to 11 mol/l is particularly useful.

The reaction mixture may be brought to a higher temperature in order to promote the evaporation of the ammonia. Preferably, the reaction mixture is heated to a temperature of from 50° C. to 150° C., advantageously from 80° C. to 130° C. and more preferably from 95° C. to 110° C. so as to evaporate the ammonia and a portion of the water. The evaporation of the ammonia makes it possible to prevent the formation of by-products that are potentially troublesome in the subsequent steps of the process.

The ammonia evolved is advantageously reused in step (ii), either as is, or after dissolving in water. The aqueous solution rich in sodium bromide recovered generally has a pH of from 9 to 13, and preferably 9.5 to 11.5.

Step (v)

In this step, the aqueous solution rich in sodium bromide obtained in the preceding step is subjected to one or more purification steps in order to eliminate the organic impurities. These impurities form a complex mixture, the content of which may be characterized by the total organic carbon (TOC). The fact of eliminating the organic impurities from the aqueous solution rich in sodium bromide makes it possible to be able to carry out step (vi) without fouling by soot which is highly detrimental to the operation of such a process.

The organic impurities present in the sodium bromide solution may be eliminated in particular by acidification, liquid-liquid extraction in an acidic or neutral medium, by adsorption or by membrane separation, or any combination of these methods. These four embodiments A-D of step (v) are described in more detail below.

Step (v) Variant A: Acidification then Decantation

In this variant, the sodium bromide solution resulting from step (iv) is acidified by addition of acid to a pH of less than 5. A less dense oily phase is then formed, which can be easily separated, for example by decantation.

The solution rich in sodium bromide resulting from step (iv) can be acidified for example by adding an aqueous solution of a strong mineral acid such as hydrochloric acid, hydrobromic acid or sulfuric acid, alone or as a mixture. Preferably, the acidified solution rich in sodium bromide has a pH of from 3 to 5 and preferably 3 to 4.5.

The formation of an oily phase rich in organic impurities is observed, which phase is less dense than the aqueous solution rich in sodium bromide. The oily phase can be separated by a means known per se, for example by decantation. This decantation may be performed for example in a static decanter or a centrifugal decanter. The purified aqueous solution rich in sodium bromide, depleted in organic compounds, may then be sent to step (vi), optionally after one or more additional purification steps according to one of the variants A-D.

The oily phase formed is eliminated directly or subjected beforehand to one or more bromide extraction steps so as to be able to recover an aqueous phase containing bromides and send it back to step (v) or to step (vi) while eliminating an oily phase containing the organic impurities.

According to an embodiment, the oily phase may be subjected to a liquid-liquid extraction, for example with a concentrated aqueous saline solution, in order to extract more bromides. Particularly preferred is extraction by means of a sodium chloride solution, preferably such a solution having a concentration of from 1 mol/l to 6 mol/l. A bromide-containing aqueous phase is recovered which is sent back to step (v) or to step (vi) and an oily phase is recovered which is eliminated.

As a variant, the extraction of the bromides from the oily phase may be carried out by mixing with water and a water-immiscible liquid carboxylic acid and decantation. As such immiscible carboxylic acids, mention may be made of heptanoic acid, octanoic acid, 2-ethylhexanoic acid, nonanoic acid, a fatty acid comprising 10 to 12 carbon atoms or a mixture of such acids. It is also possible to use distillation residues (light and heavy) of heptanoic acid or octanoic acid or 2-ethylhexanoic acid or nonanoic acid, preferably such residues containing at least 30% and preferably at least 50% of heptanoic acid, octanoic acid, 2-ethylhexanoic acid or nonanoic acid.

The oily phase/water/carboxylic acid weight ratio may vary from 1:0.3:0.3 to 1:3:2. This extraction is generally performed between ambient temperature and 130° C. and preferably between 50° C. and 100° C.

The extraction may be carried out for example in a stirred reactor with a step of contacting by vigorous mixing. It is also possible to use a static mixer. A bromide-depleted oily phase and a bromide-enriched aqueous solution are obtained, which phases can be separated by conventional liquid-liquid separation means, for example by decantation, carried out in a reactor or in a decanter. Alternatively, it is possible to carry out the extraction in a continuous liquid-liquid extraction column with:

injection of water into the upper part of the column;
injection of carboxylic acid and of the oily phase into the lower part of the column;
drawing off of the aqueous phase in the lower part of the column; and
drawing off of the oily phase in the upper part of the column.

The purified aqueous solution rich in sodium bromide obtained may be sent to step (v) or to step (vi), optionally after one or more additional purification steps according to one of the variants A-D.

According to another embodiment, the extraction of the bromides from the oily phase may be carried out by a step of diafiltration by dilution in water or with an aqueous sodium hydroxide solution and membrane separation. At the outlet of the diafiltration, a stream enriched in organic impurities and depleted in sodium bromide and an aqueous phase enriched in bromides and depleted in organic impurities are obtained. The stream enriched in organic impurities and depleted in bromides can be eliminated. The aqueous phase enriched in bromides and depleted in organic impurities may be sent to step (v) or to step (vi).

The membranes used and the procedure are described in variant D below.

Advantageously, the pH of the mixture may be adjusted prior to being sent to the membrane to a pH of greater than 7, preferably to 8 to 11 and preferably 9 to 10.

Step (v) Variant B: Liquid-Liquid Extraction

In this variant, the aqueous solution rich in sodium bromide resulting from step (iv) is neutralized, then subjected directly, i.e. without prior decantation, to a liquid-liquid extraction.

The aqueous solution rich in sodium bromide resulting from step (iv) can be neutralized for example by adding an aqueous solution of a strong mineral acid such as hydrochloric acid, hydrobromic acid or sulfuric acid, alone or as a mixture. Preferably, the neutralized solution rich in sodium bromide has a pH of from 3 to 10 and preferably 4 to 10.

The aqueous solution rich in sodium bromide may then be directly subjected to a liquid-liquid extraction as described above. In particular the solution rich in sodium bromide may be mixed with a water-immiscible carboxylic acid such as those mentioned above. The oily phase formed can be separated in a conventional manner, for example by decantation.

The liquid-liquid extraction can also be carried out in a stirred reactor, or in a continuous liquid-liquid extraction column with:
- injection of the solution rich in sodium bromide into the upper part of the column;
- injection of carboxylic acid into the lower part of the column;
- drawing off of the purified aqueous solution rich in sodium bromide in the lower part of the column; and
- drawing off of the oily phase in the upper part of the column.

The oily phase formed is eliminated directly or is subjected beforehand to one or more additional bromide extraction steps.

The purified aqueous solution rich in sodium bromide obtained may undergo a step of steam entrainment so as to eliminate volatile organic impurities therefrom. This steam entrainment step may be carried out in a stirred reactor or in a column.

The purified aqueous solution rich in sodium bromide obtained may be sent to step (vi), optionally after one or more additional purification steps according to one of the variants A-D.

Step (v) Variant C: Adsorption

In this variant, the aqueous solution rich in sodium bromide resulting from step (iv) is purified by contacting with an adsorbent.

A suitable adsorbent may in particular be activated carbon, an adsorbent macrocrosslinked resin, an ion-exchange resins or a mixture of ion-exchange residents, an adsorbent of silica type, of alumina type or of silica-alumina type.

The contacting may be carried out in one or more columns or else in a stirred reactor and followed by a solid-liquid separation. Advantageously, the contacting is carried out in several columns in series, in which the solid is stationary and the liquid passes through the bed of solid. When the adsorbent is saturated, the bromide-rich aqueous solution may be sent to another reactor or one or more other columns comprising a fresh adsorbent. The saturated adsorbent may be discharged and eliminated or where appropriate regenerated.

The adsorbent may be regenerated in a conventional manner, for example by means of washing with water, with a water-miscible solvent then again with water. The solvent loaded with organic impurities extracted from the adsorbent and water may be regenerated by distillation and reused.

Mention may be made, as examples of solvents, of methanol, ethanol, dimethyl sulfoxide, acetic acid or propanoic acid.

Prior to the adsorption step, the pH of the aqueous solution of sodium bromide may be adjusted, in particular to a pH of between 4 and 11 and preferably between 8 and 10.5, for example by means of an addition of acid as explained above, so as to be within the optimal range of effectiveness of the adsorbent.

The purified aqueous solution rich in sodium bromide obtained may be sent to step (vi), optionally after one or more additional purification steps according to one of the variants A-D.

Step (v) Variant D: Membrane Separation

In this variant, the aqueous solution rich in sodium bromide resulting from step (iv) is purified by membrane separation.

The membrane separation may be carried out for example by nanofiltration, by pervaporation, or by reverse osmosis.

The membranes may be made of ceramic, glass or metal, composite, or else of crosslinked or non-crosslinked polymer, or else be mixed (inorganic or organic). Membranes made of polyamide such as the MPS-34 nanofiltration membranes sold by the company Koch Membrane Systems are particular preferred.

The membrane may be operated in continuous, semi-continuous or batch mode. The stream may be frontal or tangential relative to the filter.

The aqueous solution rich in sodium bromide is sent to a membrane, which makes it possible to separate a first stream depleted in organic impurities from a second stream enriched in organic impurities.

In order to further increase the degree of recovery of the bromides, the stream enriched in organic impurities may then be subjected to a step of diafiltration by dilution in water and membrane separation. At the outlet of the diafiltration, a stream enriched in organic impurities and depleted in sodium bromide and a stream enriched in bromides and depleted in organic impurities are obtained.

The stream enriched in organic impurities and depleted in bromide can be eliminated. The stream enriched in bromide and depleted in organic impurities may be mixed with the first stream of bromides depleted in organic impurities.

Prior to passing over the membrane, the pH of the aqueous solution rich in sodium bromide may be adjusted to a pH greater than 7, preferably to 8 to 11 and preferably 9 to 10, for example by means of an addition of base, for example sodium hydroxide, or of an acid as explained above, so as to optimize the effectiveness of the membranes in terms of separation and also their service life.

As a variant, the stream enriched in organic impurities may be subjected, instead of the diafiltration step, to a bromide extraction step by means of one or more of the steps described in the variants A-C above.

The purified aqueous solution obtained after the membrane separation may then be sent to step (vi), optionally after one or more additional purification steps according to one of the variants A-D.

Step (vi)

This step aims to convert the bromides in the purified aqueous solution rich in sodium bromide obtained in the preceding step into bromine. This step is carried out by reaction of the aqueous solution with chlorine, so as to obtain bromine and an aqueous solution rich in sodium chloride.

The step may be carried out for example in a column comprising packing, with:
- injection at the top of the column of the purified aqueous solution of sodium bromide resulting from step (v),
- injection of chlorine into the lower quarter of the column;
- injection of steam at the bottom of the column so as to heat the bottom of the column to a temperature of from 70° C. to 100° C., advantageously from 90° C. to 100° C.;
- drawing off at the bottom of the column a stream composed mainly of sodium chloride and water;

recovery of bromine at the top of the column.

Advantageously, the aqueous solution of sodium bromide contains less than 2% and preferably less than 1% and more preferentially less than 0.5% of total organic carbon (TOC). Specifically, it has been observed that such a concentration makes it possible to limit the losses of bromide at the bottom of the column.

The flow rate of chlorine is advantageously adjusted so as to ensure a stoichiometric amount and preferably a molar excess of from 0 to 30%, more preferably from 5% to 20% relative to the bromides injected.

Step (vii)

This step aims to react the bromine obtained with hydrogen to form hydrogen bromide. This step is known to those skilled in the art and described for example in "*Bromine and its compounds*" published by Z. E. Jolles (London 1966) page 82, U.S. Pat. No. 2,070,263 or in "*Bromine*" from Ullmann's Encyclopedia of Industrial Chemistry, published by Wiley (2015).

More specifically, this step may be carried out by condensation of the bromine recovered at the top of the column in the preceding step, and injection in vaporized form into a tubular reactor co-currently with hydrogen brought to a high temperature, for example 500° C. to 1000° C.

Thus, hydrogen bromide is recovered that results partially or even completely from the recycling of the bromides produced in the process.

It has been discovered that there is proportionally less fouling in the hydrogen bromide synthesis reactor, in the form of soot, when the aqueous solution of bromide that enters in step (v) contains less TOC.

Step (vii)

This step aims to recycle the hydrogen bromide obtained in the preceding step to step (i).

The hydrogen bromide formed is cooled and may be reused for the hydrobromination step described in Example 1.

In certain embodiments of the process, the amount of hydrogen bromide recovered in step (vii) is less than the amount of hydrogen bromide injected in step (i). So that the hydrogen bromide produced is in an amount at least equal to the hydrogen bromide needed in step (i), a make-up of bromine element may be made at various points of the process, in particular in the form of bromine in step (vi), or in the form of bromide in step (iv) or (v) or A, B, C or D.

According to one particular embodiment, the aminocarboxylic acid of formula (I) obtained in step (iii) may undergo additional purification steps such as a dissolution followed by a liquid-liquid extraction, an adsorption, a recrystallization, a drying.

The aminocarboxylic acid optionally thus purified may be polymerized, for example by polycondensation, to the corresponding polyamide. Alternatively, it may also be used with other monomers such as for example polyethers for the manufacture of the corresponding copolymers.

The invention will be explained in more detail in the examples which follow.

EXAMPLES

Measurement of the Total Organic Carbon (TOC)

The total organic carbon is assayed by the difference between the total carbon measured by the catalytic combustion method at 680° C. with infrared detection and the inorganic carbon measured by acidification with 2N hydrochloric acid and infrared detection, by means of a Shimadzu TOC meter.

Measurement of the Loss of Bromine at the Bottom of the Bromine Synthesis Column The losses of bromine in the bromine synthesis step are quantified by relating the flow rate of bromides in the stream of brine at the bottom of the column to the flow rate of bromides injected into the column. The flow rates of bromides are calculated from the product of the mass flow rate of the stream and the mass concentration of bromides measured by argentometry, according to the following protocol: the solution to be titrated is diluted in distilled water acidified by a drop of nitric acid then titrated with an aqueous solution of silver nitrate (0.1 mol/l) using a Mettler Titrator titration device equipped with a DMi141-SC electrode.

Fouling of the Hydrogen Bromide Synthesis Reactor

The formation of soot in the hydrogen bromide synthesis reactor is detected by a qualitative visual observation after the tubular reactor has been operating for one day.

Example 1: Preparation of 11-Bromoundecanoic Acid by Hydrobromination of 10-Undecenoic Acid A benzene/toluene solvent mixture with a volume ratio of 50/50 is sent continuously to the top of an absorption column cooled to −20° C. where gaseous hydrogen bromide is injected at the bottom.

The stream of hydrogen bromide and solvent recovered at the bottom of the column is mixed with a stream of oxygen and brought into contact with a stream of 10-undecenoic acid at 50° C. in a T-shaped mixing device connected to a PFA pipe.

The weight ratios of the respective flow rates of solvent, hydrogen bromide, oxygen and 10-undecenoic acid are 6.3/0.49/0.0028/1. The volume of the pipe corresponds to a residence time of 0.4 minutes.

The reaction mixture leaving this pipe is evaporated so as to separate the benzene and toluene solvents and the excess hydrogen bromide and so as to isolate the 11-bromoundecanoic acid, which has a purity of close to 94%.

Example 2: Preparation of 11-Aminoundecanoic Acid by Ammonolysis of 11-Bromoundecanoic Acid Placed in a jacketed reactor equipped with mechanical stirring is 32% ammonium hydroxide at 0° C. Added, at atmospheric pressure, dropwise and rapidly, are 220 g of molten 11-bromoundecanoic acid at 90° C. The weight ratio between the 32% ammonium hydroxide and the 11-bromoundecanoic acid is 6/1. The temperature set point of the medium is adjusted to 22° C. then every 12 h 30 min the reaction medium is subjected to a temperature rise of 2° C. up to the sixth hold at 32° C. which also lasts 12 h 30 min.

Example 3: Separation of 11-Aminoundecanoic Acid and Treatment of the Filtrates

The reaction medium obtained in Example 2 is filtered and the cake is washed with a small amount of water. The cake is then suspended in water such that the weight of water used is 3.8 times greater than the amount of 11-bromoundecanoic acid used. The mixture is recrystallized by heating to 120° C. then cooling to 25° C. After filtration, the cake is washed with a small amount of water. The solid recovered is dried to obtain a powder of 11-aminoundecanoic acid.

All of the filtrates are collected then brought to 95° C. and evaporated under reduced pressure. The evaporation is stopped when a solids content of around 50% is reached, then cooling to 25° C. is carried out. After solid-liquid separation, the cake of 11-aminoundecanoic acid is washed with water. The filtrates from this crystallization step, comprising ammonium bromide and organic impurities in solution in water, are evaporated to a bromide concentration of around 350 g/l.

Sodium hydroxide at 50 wt % in aqueous solution is then added in an appropriate amount to reach a pH of 11 and heating to 95° C. is carried out so that the ammonia is evolved and is trapped in water. The aqueous solution recovered contains sodium bromide and organic impurities. The solution contains 3% of total organic carbon.

Example 4: Chlorine Treatment of the Sodium Bromides

In a column comprising packing, the aqueous solution of sodium bromide resulting from Example 3 above is injected continuously at the top of the column, chlorine is injected continuously into the lower quarter of the column and steam is injected continuously into the bottom of the column so as to heat the bottom of the column to 100° C. The flow rate of chlorine is adjusted so as to have a molar excess of 10% relative to the bromides injected.

A brine stream composed mainly of sodium chloride and water is recovered at the bottom of the column. The bromine recovered at the top of the column is condensed, then vaporized and injected co-currently with hydrogen into a tubular reactor brought to 900° C.

The hydrogen bromide formed is cooled and may be reused for the hydrobromination step described in Example 1.

The losses of bromine in the bromine synthesis column and the fouling of the hydrogen bromide synthesis reactor are listed in Table 1.

Example 5: Chlorine Treatment of the Sodium Bromides with Prior Elimination of the Organic Impurities (Process A)

The aqueous solution of sodium bromide obtained in Example 3 above, cooled to 25° C., is acidified with 33% hydrochloric acid so as to reach a pH of 4. The oily phase which settles is separated. The aqueous phase, which is analyzed at 0.3% total organic carbon, is then treated as in Example 4. The losses of bromine in the bromine synthesis column and the fouling of the hydrogen bromide synthesis reactor are listed in Table 1.

TABLE 1

| Example | TOC of NaBr aqueous phase [%] | Loss of bromine [%] at the bottom of the $Br_2$ synthesis column | Fouling of the HBr synthesis reactor |
|---|---|---|---|
| 4 | 3 | 3 | A lot of soot |
| 5 | 0.3 | 0.2 | No visible soot |
| 6 | 0.1 | 0.1 | No visible soot |
| 7 | 0.03 | <0.1 | No visible soot |
| 8 | 0.2 | 0.1 | No visible soot |

Example 6: Chlorine Treatment of the Sodium Bromides with Prior Elimination of the Organic Impurities (Process C)

The aqueous solution of sodium bromide from Example 3 and an Amberlite XAD 4 macro-crosslinked resin in a weight ratio of 5:1 are stirred for 15 minutes then a solid-liquid separation is carried out. The sodium bromide aqueous phase, the total organic carbon of which is 0.1%, is then treated as described in Example 4. The losses of bromine in the bromine synthesis column and the fouling of the hydrogen bromide synthesis reactor are listed in Table 1.

Example 7: Chlorine Treatment of the Sodium Bromides with Prior Elimination of the Organic Impurities (Process D)

The aqueous solution of sodium bromide from Example 3 is sent, at 50° C. and 30 bar, to a MPS-34 (Koch Membrane Systems) nanofiltration membrane. The volume concentration factor, defined as the ratio of the volume flow rate of feed to the volume flow rate of concentrate, is around 10. The average filtration flow rate measured is 6 kg/h/m². The total organic carbon measured for the permeate is 0.03%.

The amount of bromine lost in the concentrate (ratio of the amount of bromides in the concentrate to the amount of bromides in the aqueous solution of sodium bromide sent to the nanofiltration) is 5.4%.

A step of diafiltration in the same membrane is carried out on the concentrate after dilution with 0.5 volume of water per 1 volume of concentrate. The second membrane separation step makes it possible to lower the losses of bromides to 1.4% of the bromides of the aqueous solution of sodium bromide sent to the nanofiltration step.

The permeates collected are then treated as described in Example 4. The losses of bromine in the bromine synthesis column and the fouling of the hydrogen bromide synthesis reactor are listed in Table 1.

Example 8: Chlorine Treatment of the Sodium Bromides with Prior Elimination of the Organic Impurities (Process D)

The aqueous solution of sodium bromide from Example 3 is sent, at 50° C. and 30 bar, to a DK nanofiltration membrane from Suez. The average filtration flow rate measured is 24 kg/h/m². The total organic carbon measured for the permeate is 0.2%. The amount of bromine lost in the concentrate without a diafiltration step is 0.3%.

The permeate is then treated as described in Example 4. The losses of bromine in the bromine synthesis column and the fouling of the hydrogen bromide synthesis reactor are listed in Table 1.

All of the results showed that the process according to the invention makes it possible to recover a large amount of bromides in the effluents from the process for manufacturing 11-aminoundecanoic acid and 10-aminodecanoic acid, thus reducing the need to add bromine, which notably improves the economics of the process while furthermore reducing the amount of effluents.

LIST OF THE DOCUMENTS CITED

US 2009/0292073 A1
US 2005/0004326 A1
U.S. Pat. No. 8,013,251 B2
US 2017/0242372 A1

The invention claimed is:
1. A process for producing an aminocarboxylic acid of formula (I) below:

$$NH_2-CH_2-(CH_2)_n-COOH \qquad (I)$$

in which n is an integer from 7 to 12, comprising the following steps:
(i) reacting the unsaturated carboxylic acid of formula (II) below:

with hydrogen bromide (HBr) to form the ω-bromoalkanoic acid of formula (III) below:

(ii) reacting the ω-bromoalkanoic acid of formula (III) obtained with ammonia in aqueous solution to form a reaction mixture comprising the aminocarboxylic acid of formula (I) and ammonium bromide;
(iii) separating, from the reaction mixture obtained in step (ii), the aminocarboxylic acid of formula (I) and an aqueous solution containing ammonium bromide;
(iv) bringing the aqueous solution containing ammonium bromide obtained into contact with sodium hydroxide to form ammonia and an aqueous solution containing sodium bromide;
(v) purifying the aqueous solution containing sodium bromide obtained in order to eliminate the organic impurities;
(vi) bringing the purified aqueous solution containing sodium bromide obtained into contact with chlorine to form bromine and an aqueous solution containing sodium chloride;
(vii) reacting the bromine obtained with hydrogen to form hydrogen bromide; and
(viii) recycling the hydrogen bromide obtained to step (i).

2. The process according to claim 1, in which additional bromides are added to the solution containing ammonium bromide or sodium bromide of step (iv) or (v).

3. The process according to claim 1, in which additional bromine is added to the bromine obtained in step (vi).

4. The process according to claim 1, in which step (v) of purifying the aqueous solution containing sodium bromide reduces the measured Total Organic Carbon (TOC) by a factor of more than 5.

5. The process according to claim 1, in which step (vi) is performed with a purified aqueous solution containing sodium bromide having less than 2% of measured TOC.

6. The process according to claim 1, in which step (v) is carried out by acidification of the aqueous solution containing sodium bromide resulting from step (iv) followed by a decantation of the oily phase formed.

7. The process according to claim 6, in which the aqueous solution containing sodium bromide resulting from step (iv) is acidified by addition of an acid to a pH of between 3 and 5.

8. The process according to claim 6, in which step (v) comprises a subsequent step (va) in which the oily phase formed in step (v) is subjected to an extraction operation to obtain an aqueous solution enriched in sodium bromide, which is sent back to step (iv) or (vi).

9. The process according to claim 1, in which step (v) is carried out by neutralization of the aqueous solution containing sodium bromide followed by a liquid/liquid extraction.

10. The process according to claim 9, in which the aqueous solution containing sodium bromide is neutralized in step (v) to a pH between 3 and 10.

11. The process according to claim 1, in which step (v) is carried out by adsorption on an adsorbent material; a silica or an alumina or a mixture thereof; or an organic material.

12. The process according to claim 1, in which step (v) is carried out by membrane separation to form a permeate enriched in sodium bromide and depleted in organic impurities and a concentrate depleted in sodium bromide and enriched in organic impurities.

13. The process according to claim 12, in which step (v) is carried out by means of one or more nanofiltration membranes.

14. The process according to claim 12, in which step (v) comprises a subsequent step (va') in which the concentrate depleted in sodium bromide and enriched in organic impurities which is obtained in step (v) is subjected to a step of diafiltration in order to recover an aqueous solution enriched in sodium bromide and depleted in organic impurities, which solution is then mixed with the permeate resulting from step (v).

15. The process according to claim 12, in which step (v) comprises a subsequent step (vb) in which the permeate enriched in sodium bromide and depleted in organic impurities which is obtained in step (v) is subjected to a second step of membrane separation.

16. The process according to claim 14 in which step (v) comprises a subsequent step (vb') in which the permeate enriched in sodium bromide and depleted in organic impurities which is obtained in step (v) and the aqueous solution enriched in sodium bromide and depleted in organic impurities resulting from step (va') are subjected to a second step of membrane separation.

* * * * *